(12) United States Patent
Yamamoto et al.

(10) Patent No.: US 7,914,589 B2
(45) Date of Patent: Mar. 29, 2011

(54) FLUORINE-CONTAINING URETHANES

(75) Inventors: Ikuo Yamamoto, Settsu (JP); Yutaka Ohira, Tsukaba (JP); Shinichi Minami, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 700 days.

(21) Appl. No.: 11/659,229

(22) PCT Filed: Jul. 29, 2005

(86) PCT No.: PCT/JP2005/013947
§ 371 (c)(1),
(2), (4) Date: Feb. 2, 2007

(87) PCT Pub. No.: WO2006/013791
PCT Pub. Date: Feb. 9, 2006

(65) Prior Publication Data
US 2007/0245499 A1 Oct. 25, 2007

(30) Foreign Application Priority Data

Aug. 3, 2004 (JP) ................................. 2004-226549

(51) Int. Cl.
*C11D 3/00* (2006.01)
*D06M 15/263* (2006.01)
*C09J 11/06* (2006.01)
*C08J 5/12* (2006.01)
*C04B 28/36* (2006.01)
*C07C 69/63* (2006.01)
*B29D 22/00* (2006.01)
*B29D 23/00* (2006.01)
*B31B 45/00* (2006.01)
*B32B 1/08* (2006.01)
*B28B 23/00* (2006.01)
*B28B 21/00* (2006.01)
*B60R 21/16* (2006.01)
*A47G 19/22* (2006.01)

(52) U.S. Cl. ................. 8/115.51; 252/8.62; 106/287.28; 106/287.3; 106/287.32; 560/227; 428/34.2; 428/34.5; 428/36.1

(58) Field of Classification Search ................. 8/115.51; 252/8.62; 560/227; 106/287.28, 287.3, 287.32; 428/34.2, 34.5, 36.1

See application file for complete search history.

(56) References Cited

U.S. PATENT DOCUMENTS

| 3,547,894 A | 12/1970 | Smeltz |
| 3,663,604 A * | 5/1972 | Blochl .......................... 560/165 |
| 3,872,058 A | 3/1975 | Gresham |
| 3,883,596 A | 5/1975 | Hager et al. |
| 3,893,984 A | 7/1975 | Hager et al. |
| 3,899,484 A | 8/1975 | Walter |
| 3,906,049 A | 9/1975 | Hager et al. |
| 3,948,887 A | 4/1976 | Hager et al. |
| 3,976,698 A | 8/1976 | Hager |
| 4,113,748 A | 9/1978 | Hager et al. |
| 4,158,672 A | 6/1979 | Dear et al. |
| 4,504,401 A | 3/1985 | Matsuo et al. |
| 4,525,305 A * | 6/1985 | Patel .............................. 554/91 |
| 4,835,300 A | 5/1989 | Fukui et al. |
| 5,068,397 A | 11/1991 | Falk et al. |
| 5,414,111 A | 5/1995 | Kirchner |
| 5,415,111 A | 5/1995 | Lewnard et al. |
| 5,453,540 A * | 9/1995 | Dams et al. ....................... 564/96 |
| 5,565,564 A | 10/1996 | Kirchner |
| 5,567,794 A | 10/1996 | Barraud et al. |
| 2003/0051294 A1* | 3/2003 | Yamaguchi et al. ......... 8/115.51 |
| 2006/0091351 A1 | 5/2006 | Yamamoto et al. |

FOREIGN PATENT DOCUMENTS

| EP | 0 383 365 A2 | 8/1990 |
| EP | 1548001 A1 | 6/2005 |
| JP | 48-043096 A | 6/1973 |
| JP | 48043096 A | 6/1973 |
| JP | 49-059090 A | 6/1974 |
| JP | 49059090 A | 6/1974 |
| JP | 58-189283 | 11/1983 |
| JP | 59-31751 | 2/1984 |
| JP | 59-33315 | 2/1984 |
| JP | 63-45665 | 9/1988 |
| JP | 63-60021 | 11/1988 |
| JP | 2-60702 | 12/1990 |
| JP | 4-261132 A | 9/1992 |
| JP | 04261132 A | 9/1992 |
| JP | 6-016755 A | 1/1994 |
| JP | 06016755 A | 1/1994 |

(Continued)

OTHER PUBLICATIONS

Peter C. DeVisser, et al.; "A novel, base-liable flurous amine protecting group: synthesis and use as a tag in the purification of synthetic peptides" Tetrahedron Letters, vol. 44, 2003, pp. 9013-9016, XP002540438.

(Continued)

*Primary Examiner* — Lorna M Douyon
*Assistant Examiner* — Tanisha Diggs
(74) *Attorney, Agent, or Firm* — Sughrue Mion, PLLC

(57) ABSTRACT

Fluorine-containing urethanes represented by the general formula:

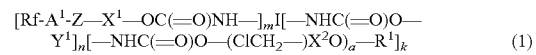

wherein I is a group derived from a polyisocyanate by removal of the isocyanato groups; Rf is perfluoroalkyl of 1 to 21 carbon atoms; $A^1$ is a direct bond or an organic group of 1 to 21 carbon atoms; $Z$ —$SO_2$—; $X^1$ is a divalent, straight-chain or branched, $C_{1-5}$ aliphatic group which may have at least one hydroxyl group; $X^2$ is a trivalent, straight-chain or branched, $C_{2-5}$ aliphatic group; $Y^1$ is a monovalent organic group which is optionally hydroxylated; and $R^1$ is hydrogen or alkyl of 1 to 10 carbon atoms.

18 Claims, No Drawings

FOREIGN PATENT DOCUMENTS

| | | |
|---|---|---|
| JP | 2001-525871 | 12/2001 |
| JP | 2001-525872 | 12/2001 |
| JP | 2001-525874 | 12/2001 |
| JP | 2002-504938 | 2/2002 |
| WO | WO 97/25308 | 7/1997 |
| WO | WO 98/51723 | 11/1998 |
| WO | WO 98/51724 | 11/1998 |
| WO | WO 98/51725 | 11/1998 |
| WO | WO 98/51726 | 11/1998 |
| WO | WO 03/048224 A1 | 6/2003 |

OTHER PUBLICATIONS

"Preliminary Risk Assessment of the Developmental Toxicity Associated with Exposure to Perfluorooctanoic Acid and its Salts"; U.S. Environmental Protection Agency Office of Pollution Prevention and Toxics Risk Assessment Division; Apr. 10, 2003.

"EPA Intensifies Scientific Investigation of a Chemical Processing Aid"; EPA Environmental News; United States Environmental Protection Agency; Monday, Apr. 14, 2003.

EPA OPPT Fact Sheet; United States Environmental Protection Agency; Apr. 14, 2003.

"Perfluorooctanoic Acid (PFOA), Fluorinated Telomers; Request for Comment, Solicitation of Interested Parties for Enforceable Consent Agreement Development, and Notice of Public Meeting"; United States Environmental Protection Agency; Federal Register; vol. 68, No. 73; Wednesday, Apr. 16, 2003; pp. 18626-18633.

* cited by examiner

FLUORINE-CONTAINING URETHANES

This is a 371 of PCT/JP2005/013947 filed Jul. 29, 2005, which claims priority from Japanese Patent Application No. 2004-226549 filed Aug. 3, 2004.

FIELD OF THE INVENTION

The present invention relates to a fluorine-containing urethane compound which impart excellent water repellency, oil repellency and soil resistance to a textile, a carpet, a paper, a non-woven fabric, a masonry, an electrostatic filter, a dust protective mask, and a part of fuel cell.

BACKGROUND ART

Hitherto, various fluorine-containing compounds, particularly fluorine-containing urethane compounds, are proposed. The fluorine-containing compounds have the advantageous effects of having excellent properties such as heat resistance, oxidation resistance and weather resistance. The fluorine-containing compounds are used as, for example, a water- and oil-repellent agent and an antifouling agent by utilizing the properties that the fluorine-containing compounds have low free energy, i.e., difficulty in adherence.

Examples of the fluorine-containing compounds, particularly fluorine-containing urethane compounds, used as the water- and oil-repellent agent are disclosed in JP-63-60021, JP-B-02-60702,
JP-B-63-45665,
U.S. Pat. No. 5,414,111,
U.S. Pat. No. 5,565,564,
EP-A-383365,
WO97/25308,
U.S. Pat. No. 3,547,894,
JP-A-2001-525871 (WO98/51723),
JP-A-2001-525872 (WO98/51726),
JP-A-2001-525874 (WO98/51724),
JP-A-2002-504938 (WO98/51725), and
WO03/048224.

The carbon number of the fluoroalkyl group in the fluorine-containing urethane compound used in Examples of these publications is usually 8. When the fluoroalkyl group having at most 6 carbon atoms is used, sufficient water- and oil-repellency and soil resistance are not exhibited.

Recent study results (EPA Report "PRELIMINARY RISK ASSESSMENT OF THE DEVELOPMENTAL TOXICITY ASSOCIATED WITH EXPOSURE TO PERFLUOROOCTANOIC ACID AND ITS SALTS" (http://www.epa.gov/opptintr/pfoa/pfoara.pdf)) and the like clarify that a PFOA (perfluorooctanoic acid) doubtfully has a potential risk of environmental load. EPA (Environmental Protection Agency of USA) announced on Apr. 14, 2003 that the EPA intensifies the scientific investigation on PFOA.

On the other hand, Federal Register (FR Vol. 68, No. 73/Apr. 16, 2003 [FRL-2303-8]) (http://www.epa.gov/opptintr/pfoa/pfoafr.pdf), EPA Environmental News for release Monday April, 2003 "EPA INTENSIFIES SCIENTIFIC INVESTIGATION OF A CHEMICAL PROCESSING AID" (http://www.epa.gov/opptintr/pfoa/pfoaprs.pdf), and EPA OPPT FACT SHEET Apr. 14, 2003 (http://www.epa.gov/opptintr/pfoa/pfoafacts.pdf) announced that a "telomer" may possibly metabolize or decompose to PFOA. It is also announced that the "telomer" is used in a large number of commercial products including fire fighting foams, care products and cleaning products as well as soil, stain and grease resistant coating on carpets, textiles, paper, and leather.

DISCLOSURE OF THE INVENTION

Problems to be Solved by the Invention

An object of the present invention is to provide a surface treatment agent having excellent water- and oil-repellency and antifouling property, even if the carbon number of a fluoroalkyl group in a fluorine-containing urethane compound is at most 6.

Means for Solving the Problems

The present invention provides a fluorine-containing urethane compound of the formula:

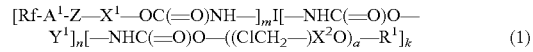
(1)

wherein I is a group remaining after an isocyanate group is removed from a polyisocyanate compound,
Rf is a perfluoroalkyl group having 1 to 21 carbon atoms,
$A^1$ is a direct bond or a divalent organic group having 1 to 21 carbon atoms,
Z is —S— or —$SO_2$—,
$X^1$ is a divalent linear or branched aliphatic group having 1 to 5 carbon atoms optionally having at least one hydroxyl group,
$X^2$ is a trivalent linear or branched aliphatic group having 2 to 5 carbon atoms,
$Y^1$ is a monovalent organic group optionally having a hydroxyl group,
$R^1$ is a hydrogen atom or an alkyl group having 1 to 10 carbon atoms,
a is the number of 1 to 20,
m is the number of 1 to 15,
n and k are the number of 0 to 14, and
the total of m, n and k is the number of 2 to 15.

The present invention also provides a composition comprising the above-mentioned fluorine-containing urethane compound, an emulsifier and water. The above-mentioned composition can be used as a treatment agent such as a surface treatment agent, a water- and oil-repellent agent and an antifouling agent.

Effects of the Invention

The present invention can give a surface treatment agent excellent in oil repellency, water repellency and antifouling property.

MODE OF CARRYING OUT THE INVENTION

The fluorine-containing urethane compound of the present invention is represented by the formula:

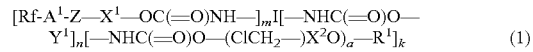
(1)

wherein I is a group remaining after an isocyanate group is removed from a polyisocyanate compound,
Rf is a perfluoroalkyl group having 1 to 21 carbon atoms, particularly 1 to 6 carbon atoms,
$A^1$ is a direct bond or a divalent organic group having 1 to 21 carbon atoms,
Z is —S— or —$SO_2$—, $X^1$ is a divalent linear or branched aliphatic group having 1 to 5 carbon atoms optionally having at least one hydroxyl group, $X^2$ is a trivalent linear or branched aliphatic group having 2 to 5 carbon atoms, $Y^1$ is a monovalent organic group optionally having a hydroxyl group, $R^1$ is a hydrogen atom or an alkyl group having 1 to 10 carbon atoms, a is the number of 1 to 20, m is the number of 1 to 15, n and k are the number of 0 to 14, and the total of m, n and k is the number of 2 to 15.

In the formula (1), I is a group remaining after the isocyanate group is removed from the polyisocyanate compound. The polyisocyanate compound is a compound having at least two isocyanate groups. The polyisocyanate compound may be an aliphatic polyisocyanate, an aromatic polyisocyanate, or derivatives of these polyisocyanates.

Examples of the aliphatic polyisocyanate, particularly an aliphatic diisocyanate are hexamethylene diisocyanate, isophorone diisocyanate, xylylene diisocyanate, hydrogenated xylylene diisocyanate, and hydrogenated dicyclohexylmethane diisocyanate. Examples of the aromatic polyisocyanate, particularly an aromatic diisocyanate are tolylene diisocyanate, diphenylmethane diisocyanate (MDI), tolidine diisocyanate and naphthalene diisocyanate.

The polyisocyanate compound is preferably a diisocyanate, polymeric MDI (diphenylmethane diisocyanate), a modified isocyanate (particularly, a trimer of diisocyanate, or an adduct between a polyhydric alcohol and a diisocyanate).

Examples of the modified isocyanate are a urethane-modified diisocyanate, an allophanate-modified diisocyanate, a biuret-modified diisocyanate, an isocyanurate-modified diisocyanate, a carbodiimide-modified diisocyanate, a uretonimine-modified diisocyanate and an acylurea diisocyanate.

The polyisocyanate compound has 2 to 15, for example, 2 to 5, particularly 2 to 3 isocyanate groups.

In the formula (1), the Rf group is a perfluoroalkyl group having 1 to 21 carbon atoms. The upper limit of carbon number of the Rf group may be 6, for example, 5, particularly 4. Examples of the Rf group include —$CF_3$, —$CF_2CF_3$, —$CF_2CF_2CF_3$, —$CF(CF_3)_2$, —$CF_2CF_2CF_2CF_3$, —$CF_2CF(CF_3)_2$, —$C(CF_3)_3$, —$(CF_2)_4CF_3$, —$(CF_2)_2CF(CF_3)_2$, —$CF_2C(CF_3)_3$, —$CF(CF_3)CF_2CF_2CF_3$, —$(CF_2)_5CF_3$, —$(CF_2)_3CF(CF_3)_2$, —$(CF_2)_4CF(CF_3)_2$, —$(CF_2)_7CF_3$, —$(CF_2)_5CF(CF_3)_2$, —$(CF_2)_6CF(CF_3)_2$, and —$(CF_2)_9CF_3$.

In the formula (1), $A^1$ is a direct bond or a divalent organic group having 1 to 21 carbon atoms. The $A^1$ group may be of the formula:

—$(CH_2)_p$—

—$CONR^{11}$—$R^{12}$—

—$CH_2C(OH)HCH_2$—

—$CH_2C(OCOR^{13})HCH_2$— or

—O—Ar—$CH_2$— wherein $R^{11}$ is hydrogen or an alkyl group having 1 to 10 carbon atoms, $R^{12}$ is an alkylene group having 1 to 10 carbon atoms, $R^{13}$ is hydrogen or a methyl group, Ar is an arylene group (having, for example, 6 to 20 carbon atoms) optionally having a substituent, and p is the number of 1 to 10.

$A^1$ may be particularly an alkylene group having 1 to 5 carbon atoms.

$X^1$ is a $C_{1-5}$ divalent linear or branched aliphatic group having no hydroxyl group, or a $C_{1-5}$ divalent linear or branched aliphatic group having at least one hydroxyl group. $X^1$ may be the alkylene group having no hydroxyl group, or the alkylene group having one, two or three hydroxyl group. Examples of $X^1$ are:

(i) an alkylene group having no hydroxyl group, selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$C(CH_3)H$—, —$C(CH_3)H$—$CH_2$—, —$CH_2$—$C(CH_3)H$—, —$CH_2$—$C(CH_3)H$—$CH_2$—, —$C(CH_3)H$—$CH_2$—$CH_2$—, —$C(CH_3)H$—$C(CH_3)H$—, —$CH_2$—$C(CH_3)_2$—$CH_2$—, —$C(CH_3)H$—$C(CH_3)H$—$CH_2$— and —$C(CH_3)H$—$CH_2$—$C(CH_3)H$—, and (ii) an alkylene group having a hydroxyl group, selected from the group consisting of —C(OH)H—, —$C(OH)HCH_2$—, —$CH_2C(OH)H$—, —$C(OH)HC(OH)H$—, —$C(OH)HCH_2CH_2$—, —$CH_2C(OH)HCH_2$—, —$CH_2CH_2C(OH)H$—, —$C(OH)HC(OH)HCH_2$—, —$C(OH)HCH_2C(OH)H$—, —$CH_2C(OH)HC(OH)H$—, —$CH_2C(OH)_2CH_2$— and —$C(OH)HC(OH)HC(OH)H$—.

The -$A^1$-Z—$X^1$— group in the formula (1) acts as a spacer. Specific examples of the spacer include the followings:

—S—$(CH_2)_2$—

—S—$(CH_2)_3$—

—$SO_2$—$(CH_2)_2$—

—$SO_2$—$(CH_2)_3$—

—$(CH_2)_2$—S—$(CH_2)_2$—

—$(CH_2)_2$—S—$(CH_2)_3$—

—$(CH_2)_2$—$SO_2$—$(CH_2)_2$—

—$(CH_2)_2$—$SO_2$—$(CH_2)_3$—

—S—$CH_2C(OH)HCH_2$—

—$SO_2$—$CH_2C(OH)HCH_2$—

—$(CH_2)_2$—S—$CH_2C(OH)HCH_2$—

—$(CH_2)_2$—$SO_2$—$CH_2C(OH)HCH_2$—

$Y^1$ is a monovalent organic group optionally having a hydroxyl group. The carbon number of $Y^1$ may be from 1 to 10, for example, from 1 to 5, particularly from 1 to 3. $Y^1$ is represented by, for example, the formula:

H—$(O)_s$—$(CH_2)_t$— wherein s is 0 or 1, and t is the number of 1 to 5. Examples of $Y^1$ are $CH_3$—, $H(CH_2)_2$—, $H(CH_2)_3$—, HO—$CH_2$—, HO—$(CH_2)_2$— and HO—$(CH_2)_3$—.

$X^2$ is a trivalent linear or branched aliphatic group having 2 to 5 carbon atoms. Examples of $X^2$ are >$CHCH_2$—(—$CH_2CH<$), >$CHCH_2CH_2$—(—$CH_2CH_2CH<$),

>CHCH$_2$CH$_2$CH$_2$—(—CH$_2$CH$_2$CH$_2$CH<), and
>CHCH$_2$CH$_2$CH$_2$CH$_2$—(—CH$_2$CH$_2$CH$_2$CH$_2$CH<).

R$^1$ is a hydrogen atom or an alkyl group having 1 to 10 carbon atoms. Examples of R$^1$ which is the alkyl group are methyl, ethyl and propyl.

"a" is the number of 1 to 20. "a" may be, for example, from 2 to 15, particularly from 2 to 10.

"m" is the number of 1 to 15. "m" may be, for example, from 2 to 10, particularly from 2 to 3.

"n" and "k" are the number of 0 to 14. "n" and "k" may be, for example, from 0 to 10, particularly from 1 to 8.

The total of m, n and k is the number of 2 to 15. The total of m, n and k may be, for example, from 2 to 10, particularly from 2 to 3.

The fluorine-containing urethane compound of the present invention may be of the formula:

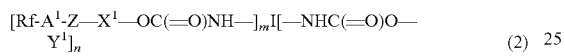

wherein I is a group remaining after an isocyanate group is removed from a polyisocyanate compound, Rf is a perfluoroalkyl group having 1 to 21 carbon atoms, A$^1$ is a direct bond or a divalent organic group having 1 to 21 carbon atoms, Z is —S— or —SO$_2$—, X$^1$ is a divalent linear or branched aliphatic group having 1 to 5 carbon atoms optionally having at least one hydroxyl group, Y$^1$ is a monovalent organic group optionally having a hydroxyl group, m is the number of 1 to 15, n is the number of 0 to 14, and the total of m and n is the number of 2 to 15; or

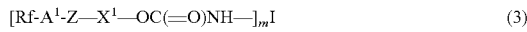

wherein I is a group remaining after an isocyanate group is removed from a polyisocyanate compound, Rf is a perfluoroalkyl group having 1 to 21 carbon atoms, A$^1$ is a direct bond or a divalent organic group having 1 to 21 carbon atoms, Z is —S— or —SO$_2$—, X$^1$ is a divalent linear or branched aliphatic group having 1 to 5 carbon atoms optionally having at least one hydroxyl group, and m is the number of 2 to 15.

Specific examples of the fluorine-containing urethane compound (1) are as follows:

[Chemical Formula 1]
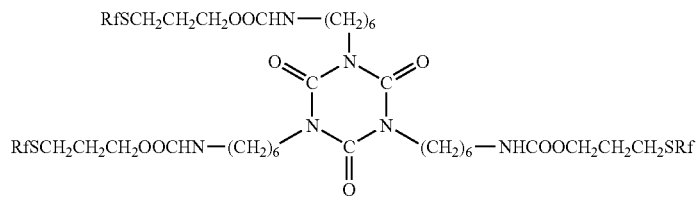

[Chemical Formula 2]
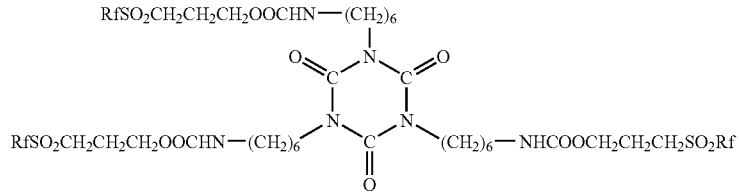

[Chemical Formula 3]
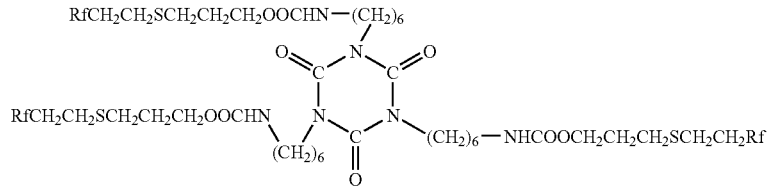

[Chemical Formula 4]
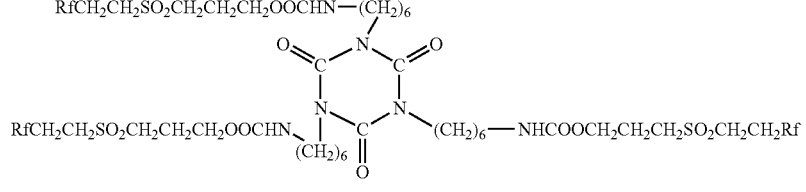

[Chemical Formula 5]
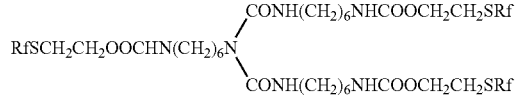

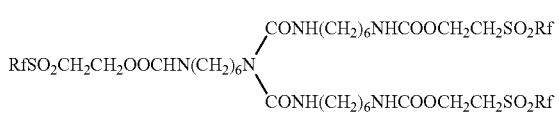

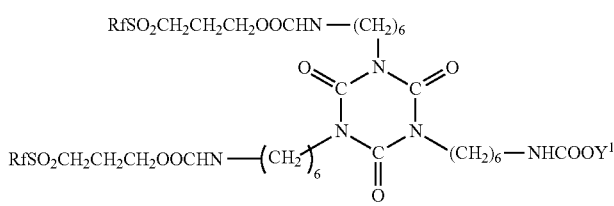

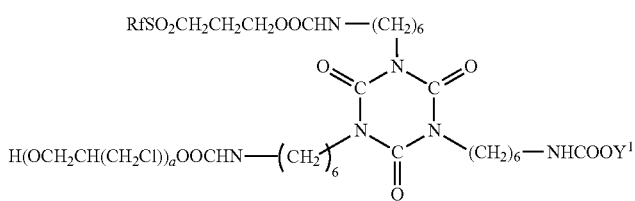

wherein Rf, $Y^1$ and a are the same as defined above.

The fluorine-containing urethane compound (1) of the present invention can be obtained, for example, by reacting a polyisocyanate compound with a fluorine-containing alcohol of the formula:

$$Rf\text{-}A^1\text{-}Z\text{-}X^1\text{-}OH \qquad (i)$$

and, optionally present, an alcohol of the formula:

$$HO\text{-}Y^1 \qquad (ii)$$

and a chlorine-containing ether alcohol of the formula:

$$HO\text{-}((ClCH_2\text{-})X^2O)_b\text{-}R^1 \qquad (iii)$$

wherein Rf, $A^1$, Z, $X^1$, $X^2$, $Y^1$, $R^1$ and a are the same as defined above.

In this reaction, the total amount of the fluorine-containing alcohol (i), the alcohol (ii) and the chlorine-containing ether alcohol (iii) is preferably from 0.5 mol to 2.0 mol, particularly from 0.8 mol to 1.5 mol, based on 1 mol of isocyanate group in the polyisocyanate compound. The alcohol (ii) and the chlorine-containing ether alcohol (iii) are a component which may be used or may not be used. This reaction is preferably conducted in the presence of a solvent at 0° C. to 150° C. for 0.1 hours to 10 hours. The solvent is an organic solvent which is inert to the isocyanate. Examples of the solvent are a hydrocarbon, a ketone and a halogenated hydrocarbon (for example, a chlorine-containing hydrocarbon). The amount of the solvent may be from 20 to 500 parts by weight, for example, from 100 to 300 parts by weight, based on 100 parts by weight of the reactants.

A catalyst is preferably used in the reaction. Examples of the catalyst are an amine (for example, a monoamine, a diamine, a triamine, an alcohol amine, and an ether amine), and an organic metal (for example, a metal salt of an organic acid such as di-n-butyl tin dilaurate). The amount of the catalyst may be from 0.001 to 0.5 parts by weight, for example, from 0.01 to 0.3 parts by weight, based on 100 parts by weight of the reactants.

The fluorine-containing alcohol (i) wherein Z is —S— can be obtained by, for example, reacting Rf-$A^1$-I (iodide) with HS—$X^1$—OH. The fluorine-containing alcohol (i) wherein Z is —$SO_2$— can be obtained by oxidizing, with a peroxide and the like, —S— in the fluorine-containing alcohol (i) wherein Z is —S— to convert —S— to —$SO_2$—.

The alcohol (ii) may be a monohydric alcohol or a polyhydric (for example, di- to penta-hydric) alcohol. Examples of the alcohol (ii) are an aliphatic alcohol and an aromatic alcohol. Specific examples of the alcohol (ii) are ethanol, propanol, ditripropylene glycol, trimethylol propane, pentaerythritol, phenol and hyrdoxytoluene.

The chlorine-containing ether alcohol (iii) can be obtained, for example, by polymerizing a chlorine-containing ether compound of the formula:

[Chemical Formula 9]

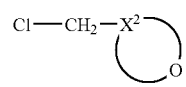

wherein $X^2$ is the same as defined above. Examples of the chlorine-containing ether compound include epichlorohydrin.

The fluorine-containing urethane compound of the present invention may be contained in a composition. The composition may be in the form of a solution or an emulsion.

The solution-type composition comprises the fluorine-containing urethane compound and a solvent. Examples of the solvent (particularly, an organic solvent) in the solution-type composition are a hydrocarbon, a ketone, and a halogenated hydrocarbon (for example, a chloride-containing hydrocarbon) and an alcohol (for example, glycol). Specific examples of the organic solvent include acetone, chloroform, HCHC225, isopropyl alcohol, pentane, hexane, heptane, octane, cyclohexane, benzene, toluene, xylene, petroleum ether, tetrahydrofuran, 1,4-dioxane, methyl ethyl ketone, methyl isobutyl ketone, ethyl acetate, butyl acetate, 1,1,2,2-tetrachloroethane, 1,1,1-trichloroethane, trichloroethylene, perchloroethylene, tetrachlorodifluoroethane and trichlorotrifluoroethane.

The emulsion-type composition comprises a fluorine-containing urethane compound, an emulsifier and water. The emulsion-type composition may further contain a water-soluble organic solvent, particularly a water-soluble organic solvent dissolving the fluorine-containing urethane compound. Examples of the water-soluble organic solvent include acetone, methyl ethyl ketone, ethyl acetate, propylene glycol, dipropylene glycol monomethyl ether, dipropylene glycol, tripropylene glycol and ethanol. The water-soluble organic solvent may be used in the amount within the range from 1 to 50 parts by weight, e.g., from 10 to 40 parts by weight, based on 100 parts by weight of water. The emulsifier may be any of nonionic and ionic (for example, cationic, anionic and amphoteric).

The amount of the fluorine-containing urethane compound may be from 0.1 to 70% by weight, for example, from 5 to 30% by weight, based on the composition. In the emulsion-type composition, relative to 100 parts by weight of the fluorine-containing urethane compound, the amount of the emulsifier may be from 0.1 to 30 parts by weight, for example, from 2 to 10 parts by weight, and the amount of the organic solvent may be from 0 to 300 parts by weight, is particularly from 10 to 200 parts by weight, for example, from 50 to 100 parts by weight. The amount of water is the balance remaining by removing the fluorine-containing urethane compound, the emulsifier and the optionally present organic solvent from the composition.

The fluorine-containing urethane compound of the present invention can be used as a treatment agent, particularly a surface treatment agent, which treats surfaces of various articles. The surface treatment agent which can modify the surfaces of articles to impart water- and/or oil-repellency and soil resistance.

The surface treatment agent of the present invention is preferably in the form of a solution, an emulsion or an aerosol. The surface treatment agent generally comprises the fluorine-containing urethane compound and a medium (particularly a liquid medium such as an organic solvent and/or water). The concentration of the fluorine-containing urethane compound in the surface treatment agent may be, for example, from 0.1 to 50% by weight.

The surface treatment agent of the present invention can be applied by a know procedure to a substrate to be treated. Usually, the surface treatment agent is diluted or dispersed with an organic solvent or water, is adhered to surfaces of the substrate by a well-known procedure such as an immersion coating, a spray coating and a foam coating, and is dried. If necessary, the surface treatment agent is applied together with a suitable crosslinking agent, followed by curing. It is also possible to add other surface treatment agents (for example, a water repellent agent and an oil repellent agent), or moth-proofing agents, softeners, antimicrobial agents, flame retardants, antistatic agents, paint fixing agents, crease-proofing agents, etc. to the surface treatment agent of the present invention. For the immersion coating, the concentration of the fluorine-containing urethane compound in an immersion treatment liquid may be from 0.05 to 10% by weight, based on the treatment liquid. For the spray coating, the concentration of the fluorine-containing urethane compound in the treatment liquid may be from 0.1 to 5% by weight, based on the treatment liquid. A stain blocker may be used together. When the stain blocker is used, it is preferable to use an anionic emulsifier or a nonionic surfactant.

The substrate to be treated with the surface-treatment agent (for example, a water- and oil-repellent agent) of the present invention include a textile (for example, a carpet and a non-woven fabric), masonry, a filter (for example, an electrostatic filter), a dust protective mask, a part of fuel cell (for example, a gaseous diffusion electrode and a gaseous diffusion support), glass, paper, wood, leather, fur, asbestos, brick., cement, metal and oxide, ceramics, plastics, a coated surface and a plaster. The textile may be particularly a carpet. The textile has various examples. Examples of the textile include animal- or vegetable-origin natural fibers such as cotton, hemp, wool and silk; synthetic fibers such as polyamide, polyester, polyvinyl alcohol, polyacrylonitrile, polyvinyl chloride and polypropylene; semi-synthetic fibers such as rayon and acetate; inorganic fibers such as glass fiber, carbon fiber and asbestos fiber; and a mixture of these fibers. The surface treatment agent of the present invention can be suitably used for carpet made from nylon and/or polypropylene.

The textile may be in any form such as a fiber, a yarn and a fabric. When the carpet is treated with the surface treatment agent of the present invention, the carpet may be formed after treating fibers or yarns with the surface treatment agent, or the formed carpet may be treated with the surface treatment agent. The fluorine-containing urethane compound of the present invention rapidly melts at a temperature (for example, about 80 to 100° C.) slightly smaller than a textile treatment temperature (generally 90 to 130° C.) to form a more homogeneous coating film on the textile, thereby giving excellent soil resistance.

The textile can be subjected to a treatment method (Exhaust process), comprising steps of:
(1) preparing a treatment liquid comprising a treatment agent and having pH of at most 7,
(2) applying the treatment liquid to the textile,
(3) thermally treating the textile with steam, and
(4) washing the textile with water and dehydrating the textile.

EXAMPLES

The following Examples are specifically illustrated but are not to be construed to limit the scope of the invention.
Water-Repellency Test A treated fabric is stored in a thermo-hygrostat having a temperature of 21° C. and a humidity of 65% for at least 4 hours. A test liquid (isopropyl alcohol (IPA), water, and a mixture thereof, as shown in Table 1) which has been also stored at 21° C. is used. The test is conducted in an air-conditioned room having a temperature of 21° C. and a humidity of 65%. A droplet of the test liquid in an amount of 0.05 mL is softly dropped on the fabric. If the droplet remains on the fabric after standing for 30 seconds, the test liquid passes the test. The water-repellency is expressed by a point corresponding to a maximum content (% by volume) of isopropyl alcohol (IPA) in the test liquid which passes the test. The water-repellency is evaluated as twelve levels which are Fail, 0, 1, 2, 3, 4, 5, 6, 7, 8, 9 and 10 in order of a poor level to an excellent level.

TABLE 1

Table 1 Water-repellency test liquid

| | (% by volume) | |
| --- | --- | --- |
| Point | Isopropyl alcohol | Water |
| 10 | 100 | 0 |
| 9 | 90 | 10 |
| 8 | 80 | 20 |
| 7 | 70 | 30 |
| 6 | 60 | 40 |
| 5 | 50 | 50 |
| 4 | 40 | 60 |
| 3 | 30 | 70 |
| 2 | 20 | 80 |
| 1 | 10 | 90 |
| 0 | 0 | 100 |

TABLE 1-continued

Table 1 Water-repellency test liquid

| | (% by volume) | |
|---|---|---|
| Point | Isopropyl alcohol | Water |
| Fail | Inferior to isopropyl alcohol 0/water 100 | |

Oil-Repellency Test

A treated fabric is stored in a thermo-hygrostat having a temperature of 21° C. and a humidity of 65% for at least 4 hours. A test liquid (shown in Table 2) which has been also stored at 21° C. is used. The test is conducted in an air-conditioned room having a temperature of 21° C. and a humidity of 65%. A droplet of the test liquid in an amount of 0.05 mL is softly dropped on the fabric. If the droplet remains on the fabric after standing for 30 seconds, the test liquid passes the test. The oil-repellency is expressed by a maximum point of the test liquid which passes the test. The oil-repellency is evaluated as nine levels which are Fail, 1, 2, 3, 4, 5, 6, 7 and 8 in order of a poor level to an excellent level.

TABLE 2

Oil-repellency test liquid

| Point | Test liquid | Surface tension (dyne/cm, 25° C.) |
|---|---|---|
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | Mixture liquid of n-Hexadecane 35/nujol 65 | 29.6 |
| 1 | Nujol | 31.2 |
| Fail | Inferior to 1 | — |

Soil Resistance Test

The soil resistance test is conducted according to AATCC Test Method 123-1989. The soil resistance is evaluated by comparing carpet samples before and after the soil resistance test by a Gray Scale for discoloration to classify 9 levels of 1, 1-2, 2, 2-3, 3, 3-4, 4, 4-5 and 5 in order of a significant discoloration level to no discloration level.

Fluorine-containing compounds were synthesized as follows.

Synthetic Example 1

Synthesis of 3-(perfluorobutylthio)propanol

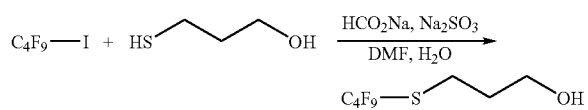

1,1,1,2,2,3,3,4,4-Nonafluoro-4-iodobutane (34.6 g, 100 mmol) was dissolved in a mixture liquid of dimethylformamide (DMF) (100 ml) and water (20 ml), and mercaptopropanol (9.2 g, 100 mmol) was added. Further, sodium formate (6.8 g, 100 mmol), and sodium sulfite heptahydrate (25.2 g, 100 mmol) were added and the mixture was stirred at room temperature for one night.

Water (250 mL) and isopropyl ether (250 mL) were added to the reaction liquid and then the mixture having two layers was separated. An aqueous layer was further extracted with isopropyl ether (100 ml×2). An organic layer was washed with 10% hydrochloric acid (125 ml), water (125 ml) and saturated saline solution (125 ml), then dried over anhydrous magnesium sulfate, filtered and distilled for solvent removal. A concentrate (3-(perfluorobutylthio)propanol) (31.0 g) was obtained. Yield: 100%.

$^1$H NMR (CDCl$_3$; Internal standard TMS δppm): 3.78 (t, 2H, $J_{H\,H}$=5.9 Hz, CH$_2$OH), 3.09 (t, 2H, $J_{H\,H}$=7.1 Hz, SCH$_2$), 1.96 (tt, 2H, $J_{H\,H}$=7.1 Hz, $J_{H\,H}$=5.9 Hz, CH$_2$CH$_2$CH$_2$)

$^{19}$F NMR (CDCl$_3$; Internal standard CFCl$_3$ δppm): −81.5 (m, 3F, CF$_3$), −88.2 (m, 2F, CF$_2$S), −121.3 (m, 2F, CF$_2$); −126.0 (m, 2F, CF$_2$).

Synthetic Example 2

Synthesis of 3-(perfluorobutylsulfonyl)propanol

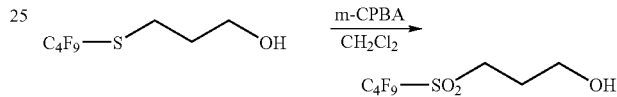

3-(Perfluorobutylthio)propanol (8.60 g, 27.6 mmol) prepared in Synthetic Example 1 was dissolved in methylene chloride (80 ml), and m-chloroperbenzoic acid (m-CPBA) (52 g, 232 mmol) was added at room temperature in two portions with stirring, the reaction vessel being equipped with a calcium chloride tube. The mixture was stirred at room temperature for 7 days. The reaction mixture was injected into a mixture of sodium thiosulfate pentahydrate (130 g) and water (200 ml), and stirred for 1 hour. Methylene chloride (100 mL) was added and an organic layer was removed and an aqueous layer was extracted with methylene chloride (50 ml). Organic layers were joined, washed with a 5% aqueous sodium hydrogen carbonate and with a saturated saline solution, and then dried over sodium sulfate. A filtrate after filtration was concentrated at reduced pressure. A residue was subjected to a silica gel column chromatography (eluting solvent: hexane/ethyl acetate (2/1)), and fractions having $R_f$ value of 0.32 [$R_f$ value (Thin Layer Chromatography (TLC)) =(Migration distance of sample)/(Migration distance of eluting solvent)] were gathered, concentrated at reduced pressure and dried at vacuum to give crystalline 3-(perfluorobutylsulfonyl)propanol (8.79 g). Yield: 91.8%.

$^1$H NMR (CDCl$_3$; Internal standard TMS δppm): 3.85 (t, 2H, $J_{H\,H}$=5.8 Hz, CH$_2$OH), 3.47 (t, 2H, $J_{H\,H}$=7.6 Hz, SO$_2$CH$_2$), 2.22 (tt, 2H, $J_{H\,H}$=7.6 Hz, $J_{H\,H}$=5.8 Hz, CH$_2$CH$_2$CH$_2$)

$^{19}$F NMR (CDCl$_3$; Internal standard CFCl$_3$ δppm): −81.2 (m, 3F, CF$_3$), −113.8 (m, 2F, CF$_2$SO$_2$), −121.8 (m, 2F, CF$_2$), −126.3 (m, 2F, CF$_2$).

Preparative Example 1

Synthesis of 1,3,5-tris[6-{3-(perfluorobutylsulfonyl)propyl carbamate}hexyl]-1,3,5-triazinan-2,4,6-trione

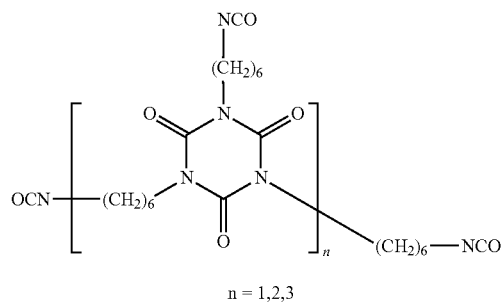

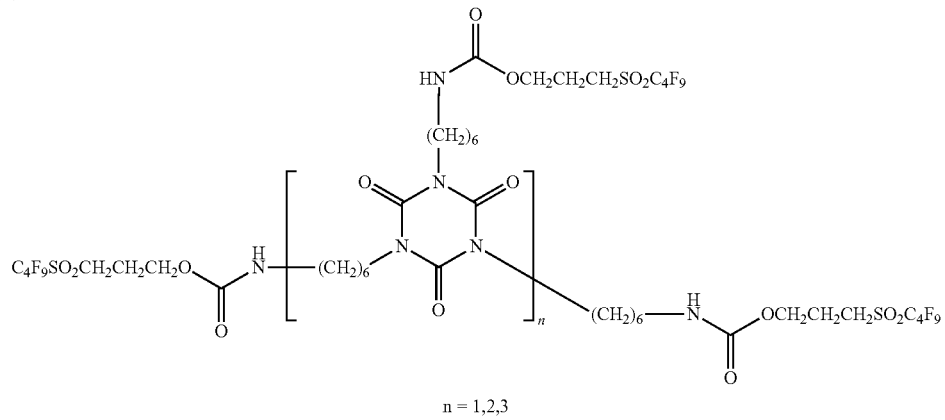

n = 1,2,3

(a mixture of compounds wherein m is 1, 2 and 3 in a weight ratio of 55:20:25)

3-(Perfluorobutylsulfonyl)propanol (8.79 g, 25.7 mmol) prepared in Synthetic Example 2 was dissolved in methyl isobutyl ketone (MIBK) (27 ml), and dibutyl tin laurate (8 mg, 0.013 mmol) was added. While the content in the reaction vessel was adjusted to the temperature of 72 to 75° C. under equipment with a calcium chloride tube, a solution of SUMI-DUR N3300 (4.95 g, NCO equivalent of 25.8 mmol) in methyl isobutyl ketone (9 ml) was dropwise added for 1.5 hours. After the dropwise addition, the mixture was stirred at 75° C. for 1 hour and the solvent was removed off at reduced pressure. Hexane was added to a residue and then a precipitated crystal was collected and vacuum dried to give a white powdery crystal (Fluorine-containing urethane compound) (13.7 g). Yield: 100%.

$^1$H NMR (CD$_3$COCD$_3$; Internal standard TMS δppm): 6.35 (broad s, 3H, NHCO), 4.20 (t, 6H, $J_{H\,H}$=6.1 Hz, C H$_2$O×3), 3.84 (t, 6H, $J_{H\,H}$=7.3 Hz, CH$_2$NHCO×3), 3.70 (t, 6H, $J_{H\,H}$=7.8 Hz, SO$_2$CH$_2$×3), 3.12 (q, 6H, $J_{H\,H}$=6.6 Hz, C H$_2$N(CO)$_2$×3), 2.25 (tt, 6H, $J_{H\,H}$=7.8 Hz, $J_{H\,H}$=6.1 Hz, CH$_2$C H$_2$CH$_2$×3), 1.56 (m×2, 12H, CH$_2$×6), 1.36 (m, 12H, CH$_2$×6)
$^{19}$F NMR (CD$_3$COCD$_3$; Internal standard CFCl$_3$ δppm): −80.6 (m, 9F, CF$_3$×3), −113.2 (m, 6F, CF$_2$SO$_2$×3), −121.0 (m, 6F, CF$_2$×3), −125.6 (m, 6F, CF$_2$×3).

Synthetic Example 3

Synthesis of 2-(3,3,4,4,5,5,6,6,6-nonafluoro-hexylthio)ethanol

3,3,4,4,5,5,6,6,6-Nonafluorohexylethyl iodide (200 g, 0.535 mol) and sodium hydroxide (25.7 g, 0.643 mol) were dissolved into water (50 ml), and then ethanol (450 ml) was added. Next, 2-mercaptoethanol (41.5 ml, 0.589 mol) was dropwise added for about 10 minutes. After the dropwise addition, the mixture was stirred at room temperature for 10 minutes. Then the mixture was refluxed for 1 hour. After the completion of the reaction, the reaction product was extracted with chloroform. After dried over anhydrous magnesium sulfate, the mixture was filtered and the solvent was removed off. After purified by distillation (88 to 89° C./5 mm Hg), an objected product was obtained at yield of 81%. (GC purity: 99%)

Synthetic Example 4

Synthesis of 2-(3,3,4,4,5,5,6,6,6-nonafluorohexyl-sulfonyl)ethanol

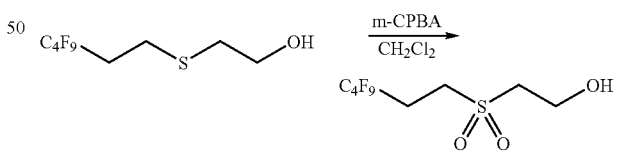

2-(3,3,4,4,5,5,6,6,6-nonafluorohexylthio)ethanol (50.0 g, 154 mmol) prepared in Synthetic Example 3 was dissolved in methylene chloride (850 ml), and m-chloroperbenzoic acid (m-CPBA) (58.6 g, 340 mmol) was added at 0° C. for 15 minutes with stirring in nitrogen atmosphere. The mixture was stirred at room temperature for one night and then methylene chloride (300 ml) was added to the reaction mixture. The reaction mixture was injected into a mixture of an aqueous saturated sodium thiosulfate pentahydrate solution (100 g) and water (100 ml). An organic layer was removed and an aqueous layer was extracted with methylene chloride (50 ml).

Organic layers were joined, washed with a saturated sodium hydrogen carbonate solution (200 ml) and with a saturated saline solution (150 ml), and then dried over magnesium sulfate. A filtrate after filtration was concentrated at reduced pressure. A residue was subjected to a silica gel column chromatography (hexane/ethyl acetate (1/1→1/2)), and fractions having $R_f$ value of 0.41 [$R_f$ value (Thin Layer Chromatography (TLC))=(Migration distance of sample)/(Migration distance of eluting solvent)] were gathered and concentrated at reduced pressure and dried at vacuum to give crystalline 2-(3,3,4,4,5,5,6,6,6-nonafluorohexylsulfonyl)ethanol (35.8 g). Yield: 65.2%.

$^1$H NMR (CDCl$_3$; Internal standard TMS δppm): 4.18 (t, 2H, $J_{H H}$=7.1 Hz, CH$_2$O), 3.41 (m, 2H, CH$_2$SO$_2$), 3.29 (t, 2H, $J_{H H}$=7.1 Hz, CH$_2$SO$_2$), 2.7 (m, 2H, CF$_2$CH$_2$)

$^{19}$F NMR (CDCl$_3$; Internal standard CFCl$_3$ δppm): −81.8 (t, J=9.7 Hz, 3F, CF$_3$), −114.7 (m, 2F, CF$_2$SO$_2$), −125.0 (m, 6F, CF$_2$), −126.9 (m, 6F, CF$_2$).

Preparative Example 2

Synthesis of 1,3,5-tris[6-(2-(3,3,4,4,5,5,6,6,6-nonafluoro-hexylsulfonyl)ethyl carbamate}hexyl]-1,3,5-triazinan-2,4,6-trione stirred at 75° C. for 1 hour and the solvent was removed at reduced pressure. Hexane was added to a residue and then a precipitated crystal was collected and vacuum dried to give a white powdery crystal (Fluorine-containing urethane compound) (15.4 g). Yield: 100%.

$^1$H NMR (CD$_3$COCD$_3$; Internal standard TMS δppm): 6.44 (broad s, 3H, NHCO), 4.46 (t, 6H, $J_{H H}$=5.7 Hz, CH$_2$O×3), 3.83 (t, 6H, $J_{H H}$=7.3 Hz, CH$_2$NHCO×3), 3.56 (t, 6H, $J_{H H}$=5.7 Hz, SO$_2$CH$_2$×3), 3.50 (m, 6H, SO$_2$CH$_2$×3), 3.13 (q, 6H, $J_{H H}$=6.8 Hz, CH$_2$N(CO)$_2$×3), 2.78 (m, 6H, CH$_2$CF$_2$×3), 1.56 (m×2, 12H, CH$_2$×6), 1.36 (m, 12H, CH$_2$×6)

$^{19}$F NMR (CD$_3$COCD$_3$; Internal standard CFCl$_3$ δppm): −80.9 (m, 9F, CF$_3$×3), −113.2 (m, 6F, CF$_2$SO$_2$×3), −123.6 (m, 6F, CF$_2$×3), −125.6 (m, 6F, CF$_2$×3).

Comparative Preparative Example 1

Synthesis of 1,3,5-tris[6-{N-methyl-N-(perfluorobutyl-sulfonamino)ethyl carbamate}hexyl]-1,3,5-triazinan-2,4,6-trione

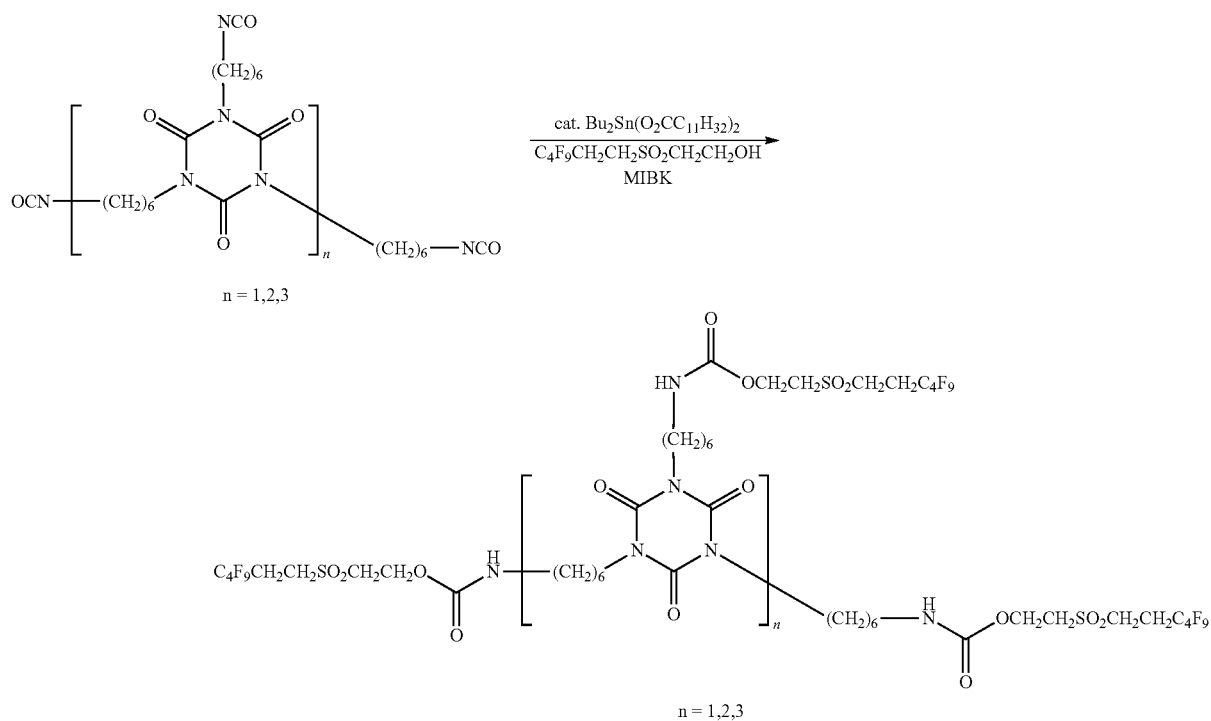

(a mixture of compounds wherein m is 1, 2 and 3 in a weight ratio of 55:20:25)

2-(3,3,4,4,5,5,6,6,6-nonafluorohexylsulfonyl)ethanol (10.0 g, 28.1 mmol) prepared in Synthetic Example 4 was dissolved in methyl isobutyl ketone (30 ml), and dibutyl tin laurate (9 mg, 0.014 mmol) was added. While the content in the reaction vessel was adjusted to the temperature of 72 to 75° C. under equipment with a calcium chloride tube, a solution of SUMIDUR N3300 (5.40 g, NCO equivalent of 28.1 mmol) in methyl isobutyl ketone (9 ml) was dropwise added for 1.5 hours. After the dropwise addition, the mixture was

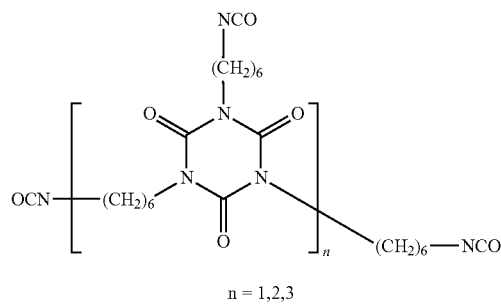

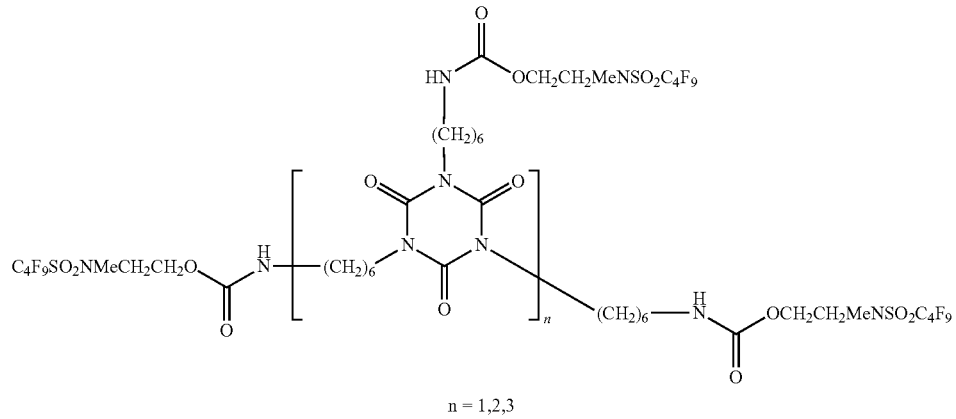

wherein Me is a methyl group.

N-methyl-N-(perfluorobutylsulfonamino)ethanol (10.0 g, 28.0 mmol) was dissolved in methyl isobutyl ketone (30 ml), and dibutyl tin laurate (9 mg, 0.015 mmol) was added. While the content in the reaction vessel was adjusted to the temperature of 72 to 75° C. under equipment with a calcium chloride tube, a solution of SUMIDUR N3300 (5.40 g, NCO equivalent of 28.0 mmol) in methyl isobutyl ketone (10 ml) was dropwise added for 1.5 hours. After the dropwise addition, the mixture was stirred at 75° C. for 1 hour and the solvent was removed at reduced pressure. Hexane was added to a residue and then a precipitated crystal was collected and vacuum dried to give a white powdery crystal (15.4 g). Yield: 100%.

$^1$H NMR (CD$_3$COCD$_3$; Internal standard TMS δppm): 6.38 (broad s, 3H, NHCO), 4.3 (broad d, 6H, CH$_2$O×3), 3.83 (t, 6H, J$_{HH}$=7.5 Hz, CH$_2$NHCO×3), 3.22 (s, 9H, NCH$_3$×3), 3.12 (q, 6H, J$_{HH}$=6.6 Hz, CH$_2$N(CO)$_2$×3), 1.56 (m×2, 12H, CH$_2$×6), 1.36 (m, 12H, CH$_2$×6)

$^{19}$F NMR (CD$_3$COCD$_3$; Internal standard CFCl$_3$ δppm): −80.7 (m, 9F, CF$_3$×3), −112.0 (m, 6F, CF$_2$SO$_2$N×3), −121.1 (m, 6F, CF$_2$×3), −125.6 (m, 6F, CF$_2$×3).

Comparative Preparative Example 2

Synthesis of 1,3,5-tris{6-(3,3,4,4,5,5,6,6,6-nonafluoro-hexylcarbamate)hexyl}-1,3,5-triazinan-2,4,6-trione

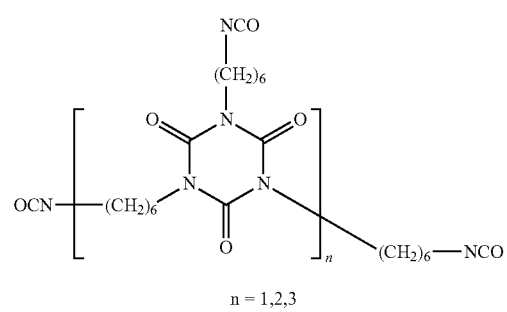

-continued

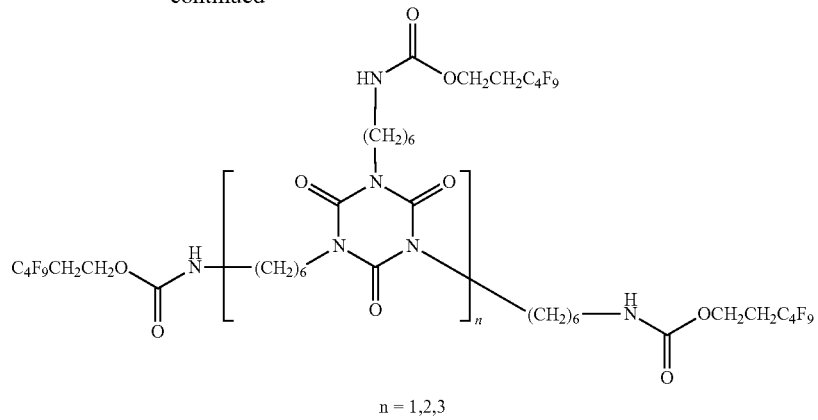

n = 1,2,3

Perfluorobutylethanol (26.4 g, 100 mmol) was dissolved in methyl isobutyl ketone (107 ml), and dibutyl tin laurate (32 mg, 0.051 mmol) was added. While the content in the reaction vessel was adjusted to the temperature of 72 to 75° C. under equipment with a calcium chloride tube, a solution of SUMIDUR N3300 (19.2 g, NCO equivalent of 100 mmol) in methyl isobutyl ketone (32 ml) was dropwise added for 3.5 hours. After the dropwise addition, the mixture was stirred at 75 to 76° C. for 2 hours and the solvent was removed at reduced pressure. The mixture was vacuum dried to give viscous white opaque liquid (45.6 g). Yield: 100%.

$^1$H NMR (CD$_3$COCD$_3$; Internal standard TMS δppm): 6.38 (broad s, 3H, NHCO), 4.33 (t, 6H, $J_{H\ H}$=6.2 Hz, C H$_2$O×3), 3.84 (t, 6H, $J_{H\ H}$=7.2 Hz, CH$_2$NHCO×3), 3.13 (q, 6H, $J_{H\ H}$=6.3 Hz, CH$_2$N(CO)$_2$×3), 2.6 (m, 6H, CH$_2$CF$_2$×3), 1.56 (m×2, 12H, CH$_2$×6), 1.36 (m, 12H, CH$_2$×6)

$^{19}$F NMR (CD$_3$COCD$_3$; Internal standard CFCl$_3$ δppm): −81.0 (m, 9F, CF$_3$×3), −113.3 (m, 6F, CF$_2$×3), −124.2 (m, 6F, CF$_2$×3), −125.7 (m, 6F, CF$_2$×3).

Example 1

The fluorine-containing urethane compound (2 g) synthesized in Preparative Example 1 and methyl isobutyl ketone (MIBK) (2 g) were mixed and heated at 75° C. for 10 minutes. In another vessel, pure water (15.6 g), polyoxyethylenealkyl ether (nonionic emulsifier) (0.24 g) and sodium alpha-olefin sulfonate (anionic emulsifier) (0.1 g) were mixed and warmed at 75° C. to 80° C. for 10 minutes. These two liquids were mixed and emulsified by a ultrasonic emulsifier.

Water (92.1 g) was added to the resultant emulsion (7.9 g) to give the total amount of 100 g which was a treatment liquid. This treatment liquid was used for spray treatment on a carpet (20 cm×20 cm, nylon 6, loop pile (density of 26 oz/yd$^2$)) at WPU (Wet Pick Up) of 30% (when 30 g of the liquid is positioned in 100 g of carpet, WPU is 30%). Then the thermal curing was conducted at 120° C. for 10 minutes.

Next, the water repellency test, the oil repellency test and the soil resistance test were conducted. The results are shown in Table 3.

Example 2

The fluorine-containing urethane compound synthesized in Preparative Example 2 was emulsified in the same manner as in Example 1. Water (91.2 g) was added to the resultant emulsion (8.8 g) to give the total amount of 100 g which was a treatment liquid. This repellent agent was used for treating a carpet in the same manner as in Example 1.

Next, the water repellency test, the oil repellency test and the soil resistance test were conducted. The results are shown in Table 3.

Example 3

The fluorine-containing urethane compound (2 g) synthesized in Preparative Example 1 and methyl isobutyl ketone (MIBK) (2 g) were mixed and heated at 75° C. to 80° C. for 10 minutes. In another vessel, pure water (15.6 g), polyoxyethylenealkyl ether (nonionic emulsifier) (0.24 g) and sodium alpha-olefin sulfonate (anionic emulsifier) (0.1 g) were mixed and warmed at 75° C. to 80° C. for 10 minutes. These two liquids were mixed and emulsified by ultrasonic emulsifier.

Water was added to the resultant emulsion (3.8 g) and a stain blocking agent A (a mixture of a phenol/formaldehyde condensate and polyacrylic acid in a weight ratio of 50:50) (6 g) to give the total amount of 1000 g which was a dilution liquid. A 10% aqueous sulfamic acid solution was added to the dilution liquid to adjust the pH to 1.5, thereby giving a treatment liquid.

A carpet (20 cm×20 cm, nylon 6, cut pile, density of 32 oz/yd$^2$), which was washed with water and squeezed, at WPU (Wet Pick Up) of about 25% (when 25 g of the liquid is positioned in 100 g of carpet, WPU is 25%), was immersed in the treatment liquid for 30 seconds and squeezed to give WPU (Wet Pick Up) of 30% (when 30 g of the liquid is positioned on 100 g of carpet, WPU is 30%). The treated carpet has the fluorine-content of 300 ppm. A normal pressure steamer treatment (100 to 107° C.) was conducted for 90 seconds under the state that a pile surface of the carpet is upward. Next, the carpet was rinsed with water (10 L) and subjected to centrifugal dehydration to give WPU of about 25%. Finally, the thermal curing was conducted at 110° C. for 10 minutes.

Next, the water repellency test, the oil repellency test and the soil resistance test were conducted. The results are shown in Table 4.

Example 4

The fluorine-containing urethane compound synthesized in Preparative Example 2 was emulsified in the same manner as in Example 3. Water was added to the resultant emulsion (3.8 g) and a stain blocking agent A (6 g) to give the total amount of 1000 g. A 10% aqueous sulfamic acid solution was added to the dilution liquid to adjust the pH to 1.5, thereby giving a treatment liquid. This repellent agent was used for treating a carpet in the same manner as in Example 3.

Next, the water repellency test, the oil repellency test and the soil resistance test were conducted. The results are shown in Table 4.

Comparative Example 1

The fluorine-containing urethane compound synthesized in Comparative Preparative Example 1 was emulsified in the same manner as in Example 1. Water (91.7 g) was added to the resultant emulsion (8.3 g) to give the total amount of 100 g which was a treatment liquid. This repellent agent was used for treating a carpet in the same manner as in Example 1.

Next, the water repellency test, the oil repellency test and the soil resistance test were conducted. The results are shown in Table 3.

Comparative Example 2

The fluorine-containing urethane compound synthesized in Comparative Preparative Example 2 was emulsified in the same manner as in Example 1. Water (92.7 g) was added to the resultant emulsion (7.2 g) to give the total amount of 100 g which was a treatment liquid. This repellent agent was used for treating a carpet in the same manner as in Example 1.

Next, the water repellency test, the oil repellency test and the soil resistance test were conducted. The results are shown in Table 3.

Comparative Example 3

Water (97.7 g) was added to UNIDINE TG-571 (2.3 g) manufactured by Daikin Industries, Ltd. to give the total amount of 100 g which was a treatment liquid. This repellent agent was used for treating a carpet in the same manner as in Example 1.

Next, the water repellency test, the oil repellency test and the soil resistance test were conducted. The results are shown in Table 4.

Comparative Example 4

The fluorine-containing urethane compound synthesized in Comparative Preparative Example 1 was emulsified in the same manner as in Example 3. Water was added to the resultant emulsion (3.8 g) and a stain blocking agent A (6 g) to give the total amount of 1000 g. A 10% aqueous sulfamic acid solution was added to the dilution liquid to adjust the pH to 1.5, thereby giving a treatment liquid. This repellent agent was used for treating a carpet in the same manner as in Example 3.

Next, the water repellency test, the oil repellency test and the soil resistance test were conducted. The results are shown in Table 4.

Comparative Example 5

The fluorine-containing urethane compound synthesized in Comparative Preparative Example 2 was emulsified in the same manner as in Example 3. Water was added to the resultant emulsion (3.8 g) and a stain blocking agent A (6 g) to give the total amount of 1000 g. A 10% aqueous sulfamic acid solution was added to the dilution liquid to adjust the pH to 1.5, thereby giving a treatment liquid. This repellent agent was used for treating a carpet in the same manner as in Example 3.

Next, the water repellency test, the oil repellency test and the soil resistance test were conducted. The results are shown in Table 4.

Comparative Example 6

Water was added to UNIDINE TG-571 (3.8 g) manufactured by Daikin Industries, Ltd. and a stain blocking agent A (6 g) to give the total amount of 1000 g. A 10% aqueous sulfamic acid solution was added to the dilution liquid to adjust the pH to 1.5, thereby giving a treatment liquid. This repellent agent was used for treating a carpet in the same manner as in Example 3.

Next, the water repellency test, the oil repellency test and the soil resistance test were conducted. The results are shown in Table 4.

TABLE 3

Table 3

| | | Water repellency | Oil repellency | Soil resistance |
|---|---|---|---|---|
| Example 1 | Preparative Example 1 | 2 | 2 | 5 |
| Example 2 | Preparative Example 2 | 2 | 2 | 5 |
| Comparative Example 1 | Comparative Preparative Example 1 | 2 | 1 | 4 |
| Comparative Example 2 | Comparative Preparative Example 2 | Fail | Fail | 3 |
| Comparative Example 3 | UNIDINE TG-571 manufactured by Daikin Industries, Ltd. | 8 | 6 | 2 |

TABLE 4

Table 4

| | | Water repellency | Oil repellency | Soil resistance |
|---|---|---|---|---|
| Example 3 | Preparative Example 1 | 2 | 2 | 5 |
| Example 4 | Preparative Example 2 | 2 | 2 | 5 |
| Comparative Example 4 | Comparative Preparative Example 1 | 2 | 1 | 4 |
| Comparative Example 5 | Comparative Preparative Example 2 | 1 | 1 | 3 |
| Comparative Example 6 | UNIDINE TG-571 manufactured by Daikin Industries, Ltd. | 3 | 2 | 2 |

The invention claimed is:

1. A fluorine-containing urethane compound of the formula:

[Rf-A$^1$-Z—X$^1$—OC(=O)NH—]$_m$I [—NHC(=O) O—Y$^1$]$_n$ [—NHC(=O)O—((ClCH$_2$—)X$^2$O)$_a$— R$^1$]$_k$     (1)

wherein I is a group remaining after an isocyanate group is removed from a polyisocyanate compound and the polyisocyanate compound constituting the I group is an aliphatic polyisocyanate, Rf is a perfluoroalkyl group having 1 to 21 carbon atoms, A$^l$ is a direct bond or a divalent organic group having 1 to 21 carbon atoms,
Z is —SO$_2$—,
X$^1$ is a divalent linear or branched aliphatic group having 1 to 5 carbon atoms optionally having at least one hydroxyl group,
X$^2$ is a trivalent linear or branched aliphatic group having 2 to 5 carbon atoms,
Y$^1$ is a monovalent organic group optionally having a hydroxyl group,
R$^1$ is a hydrogen atom or an alkyl group having 1 to 10 carbon atoms,
a is the number of 1 to 20,
m is the number of 1 to 15,
n and k are the number of 0 to 14, and
the total of m, n and k is the number of 2 to 15.

2. The fluorine-containing urethane compound according to claim 1, wherein the polyisocyanate compound constituting the I group is a diisocyanate or a modified isocyanate.

3. The compound according to claim 1, wherein the A$^1$ group is of the formula:
—(CH$_2$)$_p$—
—CONR$^{11}$—R$^{12}$—
—CH$_2$C(OH)HCH$_2$—
—CH$_2$C(OCOR$^{13}$)HCH$_2$— or
—O—Ar—CH$_2$—
wherein R$^{11}$ is hydrogen or an alkyl group having 1 to 10 carbon atoms,
R$^{12}$ is an alkylene group having 1 to 10 carbon atoms,
R$^{13}$ is hydrogen or a methyl group,
Ar is an arylene group (having, for example, 6 to 20 carbon atoms) optionally having a substituent, and
p is the number of 1 to 10.

4. The compound according to claim 1, wherein the X$^1$ group is:
(i) an alkylene group having no hydroxyl group, selected from the group consisting of —CH$_2$—, —CH$_2$ CH$_2$—, —CH$_2$ CH$_2$ CH$_2$—, —CH$_2$ CH$_2$ CH$_2$ CH$_2$—, —CH$_2$ CH$_2$ CH$_2$ CH$_2$, —C(CH$_3$)H—, —C(CH$_3$)H—CH$_2$—, —CH$_2$—C(CH$_3$)H—, —CH$_2$—C(CH$_3$)H—CH$_2$—, —C(CH$_3$)H, —CH$_2$—CH$_2$—, —C(CH$_3$)H—C(CH$_3$)H—, —CH$_2$—C(CH$_3$)$_2$—CH$_2$—, —C(CH$_3$)H—C(CH$_3$)H—CH$_2$— and —C(CH$_3$)H—CH$_2$—C(CH$_3$)H—, or
(ii) an alkylene group having a hydroxyl group, selected from the group consisting of —C(OH)H—, —C(OH)HCH$_2$—, —CH$_2$ C(OH)H—, —C(OH)HC(OH)H—, —C(OH)HCH$_2$ CH$_2$—, —CH$_2$ C(OH)HCH$_2$—, —CH$_2$ CH$_2$ C(OH)H—, —C(OH)HC(OH)HCH$_2$—, —C(OH)HCH$_2$ C(OH)H—, —CH$_2$ C(OH)HC(OH)H—, —CH$_2$ C(OH)$_2$ CH$_2$— and —C(OH)HC(OH)HC(OH)H—.

5. The fluorine-containing urethane compound according to claim 1, which is of the formula:

[Rf-A$^1$-Z—X$^1$—OC(=O)NH—]$_m$I [—NHC(=O)O—Y$^1$]$_n$ (2)

wherein I is a group remaining after an isocyanate group is removed from a polyisocyanate compound and the polyisocyanate compound constituting the I group is an aliphatic polyisocyanate,
Rf is a perfluoroalkyl group having 1 to 21 carbon atoms,
A$^l$ is a direct bond or a divalent organic group having 1 to 21 carbon atoms,
Z is —SO$_2$—,
X$^1$ is a divalent linear or branched aliphatic group having 1 to 5 carbon atoms optionally having at least one hydroxyl group,
Y$^1$ is a monovalent organic group optionally having a hydroxyl group,
m is the number of 1 to 15,
n is the number of 0 to 14, and
the total of m and n is the number of 2 to 15.

6. The fluorine-containing urethane compound according to claim 1, which is of the formula:

[Rf-A$^l$-Z—X$^1$—OC(=O)NH—]$_m$I (3)

wherein I is a group remaining after an isocyanate group is removed from a polyisocyanate compound and the polyisocyanate compound constituting the I group is an aliphatic polyisocyanate,
Rf is a perfluoroalkyl group having 1 to 21 carbon atoms,
A$^l$ is a direct bond or a divalent organic group having 1 to 21 carbon atoms,
Z is —SO$_2$—,
X$^1$ is a divalent linear or branched aliphatic group having 1 to 5 carbon atoms optionally having at least one hydroxyl group, and
m is the number of 2 to 15.

7. The fluorine-containing urethane compound according to claim 1, wherein the Rf group is a perfluoroalkyl group having 1 to 6 carbon atoms.

8. A composition comprising the fluorine-containing urethane compound according to claim 1, an emulsifier and water.

9. A treatment agent comprising the composition according to claim 8.

10. The treatment agent according to claim 9 which is a surface treatment agent.

11. The treatment agent according to claim 9 which is a water- and oil-repellent agent or an antifouling agent.

12. A method of treating a substrate with a treatment agent, said treatment agent comprising the fluorine-containing urethane compound as claimed in claim 1, an emulsifier and water, and said method comprising applying the treatment agent to the substrate.

13. The method according to claim 12, wherein a textile is subjected to a treatment comprising steps of:
(1) preparing a treatment liquid comprising the treatment agent and having pH of at most 7,
(2) applying the treatment liquid to the textile,
(3) thermally treating the textile with steam, and
(4) washing the textile with water and dehydrating the textile.

14. A textile having a coating containing the fluorine-containing urethane compound as claimed in claim 1 deposited on the textile.

15. The method of claim 12, wherein the substrate comprises paper.

16. Paper having a coating containing the fluorine-containing urethane compound as claimed in claim 1 deposited on the paper.

17. The method of claim 12, wherein the substrate comprises a non-woven fabric.

18. A non-woven fabric having a coating containing the fluorine-containing urethane compound as claimed in claim 1 deposited on the non-woven fabric.

* * * * *